United States Patent [19]

Saloheimo et al.

[11] Patent Number: 4,786,373
[45] Date of Patent: Nov. 22, 1988

[54] VOLTAMMETRIC METHOD OF MEASURING

[75] Inventors: Kari M. O. Saloheimo; Seppo V. Rantapuska, both of Espoo, Finland

[73] Assignee: Outokumpu Oy, Helsinki, Finland

[21] Appl. No.: 50,056

[22] Filed: May 13, 1987

Related U.S. Application Data

[63] Continuation-in-part of Ser. No. 844,846, Mar. 27, 1986, abandoned, which is a continuation-in-part of Ser. No. 684,748, Dec. 2, 1984, abandoned.

[30] Foreign Application Priority Data

Dec. 29, 1983 [FI] Finland ................ 834847

[51] Int. Cl.$^4$ ............................................ G01N 27/46
[52] U.S. Cl. .................................. 204/1 T; 204/402; 204/434
[58] Field of Search .............. 204/1 T, 400, 402, 409, 204/DIG. 9, 434; 73/861.12

[56] References Cited

U.S. PATENT DOCUMENTS

| | | | |
|---|---|---|---|
| 3,479,873 | 11/1969 | Hermanns | 204/222 X |
| 3,658,679 | 4/1972 | Stansell et al. | 204/409 |
| 3,664,191 | 5/1972 | Hermanns | 204/222 X |
| 3,676,321 | 7/1972 | Cummings et al. | 204/409 X |
| 3,904,487 | 9/1975 | Lieberman et al. | 204/433 X |
| 4,033,830 | 7/1977 | Fletcher, III | 204/1 T X |
| 4,083,754 | 4/1978 | Outsuka et al. | 204/433 X |
| 4,172,770 | 10/1979 | Semersky et al. | 204/409 X |
| 4,216,671 | 8/1980 | Kurland | 204/1 T X |

OTHER PUBLICATIONS

Bard et al., "Electrochemical Methods", John-Wiley & Son, 1980, pp. 136-141.

Primary Examiner—John F. Niebling
Assistant Examiner—Nam X. Nguyen
Attorney, Agent, or Firm—Dellett, Smith-Hill and Bedell

[57] ABSTRACT

A stripping analysis method comprises a preelectrolysis step during which liquid to be analyzed is introduced into a measurement cell at a pulsating rate, a working electrode is vibrated at an ultrasonic frequency, and the voltage potential between the working electrode and a reference electrode is adjusted to a level which allows the substances to be determined to be deposited on the working electrode. After the preelectrolysis step is a stripping step during which the voltage potential between the working electrode and the reference electrode is scanned through the potential range where the substances to be determined are dissolved back to the liquid and current is measured while the liquid in the measurement cell remains essentially undisturbed. The method also comprises an elimination step during which the voltage potential between the working electrode and the reference electrode is adjusted to a level at which the working electrode is regenerated. The products of the measurement step are removed from the cell by vibrating the working electrode at an ultrasonic frequency and thereby disturbing the liquid in the cell, and introducing liquid into the cell at a non-pulsating rate and thereby displacing liquid from the cell.

3 Claims, 3 Drawing Sheets

VOLTAMMETRIC METHOD OF MEASURING

CROSS-REFERENCE TO RELATED APPLICATION

This is a continuation-in-part of co-pending patent application Ser. No. 844,846 filed Mar. 27, 1986, now abandoned, which itself was a continuation-in-part of co-pending patent application Ser. No. 684,748 filed Dec. 2, 1984 now abandoned.

BACKGROUND OF THE INVENTION

The present invention relates to the determination of the concentration of substances of interest in a liquid, by stripping analysis. More particularly, the invention relates to a method of stripping analysis where ultrasound is conducted on the working electrode.

Stripping analysis is carried out in a measurement cell having three electrodes, namely a working electrode, a counter electrode and a reference electrode. The three electrodes contact a sample of a liquid under test (which may be in the form of a slurry). The potential difference between the working electrode and the reference electrode is controlled and the current that flows through the working electrode, due to oxidation/reduction reactions of the ions in the liquid under test, is measured. The potentials at which current peaks are observed are characteristic of the substances that are present in the liquid under test, and the size of a current peak indicates the concentration of the particular substance in the liquid under test.

Stripping analysis is generally used for measuring the concentration of anions and cations of substances of interest in a liquid. In most cases the working electrode is a hanging mercury drop electrode or a mercury film electrode. These are best suited for analyzing mercury-soluble metals. Measurements of other metals, such as iron, nickel and cobalt, are often carried out by means of electrodes made of solid materials. However, the use of solid working electrodes brings forth several problems. In many cases chemical changes of the electrode material occur on the electrode surface and a large amount of hydrogen is created in comparison to a mercury electrode, causing interfering background current.

The influence of ultrasound on an electrode and on the electrolyte surrounding it using different measurement methods is described for instance in Soviet Union Pat. No. 219,860. The said Soviet Union patent employs an ultrasound field in a polarographic measuring method, and the purpose of the ultrasonic field is to keep the electrode clean and to improve measuring sensitivity owing to the advantageous agitating effect caused by the field. Ultrasound is also used in an amperometric measuring method, U.S. Pat. No. 4,033,830, for keeping the necessary counter- and measuring electrodes clean. As a conclusion, the aforementioned patents use ultrasound only for improving the sensitivity of the electrodes and for keeping the electrodes clean. When employed in this fashion, however, ultrasound does not essentially improve the conditions of the analysis carried out by solid electrodes.

The purpose of the present invention is to eliminate some of the drawbacks in the prior art and to achieve a new and better method for the voltammetric measurement of the component contents of a liquid phase by utilizing ultrasound during the measurement.

SUMMARY OF THE INVENTION

In a preferred measurement method embodying the invention, a liquid is analyzed using a measurement device that comprises a wall structure defining a measurement cell for receiving liquid to be analyzed, and also comprises a working electrode and an reference electrode that contact liquid in the cell. The method comprises a preelectrolysis step which is followed in order by a stripping step and an elimination step. During the preelectrolysis step, liquid to be analyzed is introduced into the measurement cell at an irregular, or pulsating, rate, the working electrode is vibrated at an ultrasonic frequency, and the voltage potential between the working electrode and the reference electrode is set to a level, which allows electroactive substances to be deposited on the working electrode. In the stripping step, the voltage potential between the working electrode and the reference electrode is scanned through the potential range where the substances accumulated on the working electrode are dissolved again to the liquid. The current peaks arising from the oxidation/reduction reactions are measured while the liquid in the measurement cell remains essentially undisturbed. In the elimination step, the voltage potential between the working electrode and the reference electrode is set to a level held essentially constant and where the residues remaining after the measurement step are removed from the cell by vibrating the working electrode at an ultrasonic frequency and thereby disturbing the liquid in the cell, and introducing liquid into the cell at an irregular, or pulsating, rate and thereby displacing liquid from the cell.

BRIEF DESCRIPTION OF THE DRAWINGS

The invention is described in more detail below, with reference to the appended drawings where

In FIGS. 1 and 2, corresponding elements are indicated by like reference numerals.

DETAILED DESCRIPTION

Figure 1:
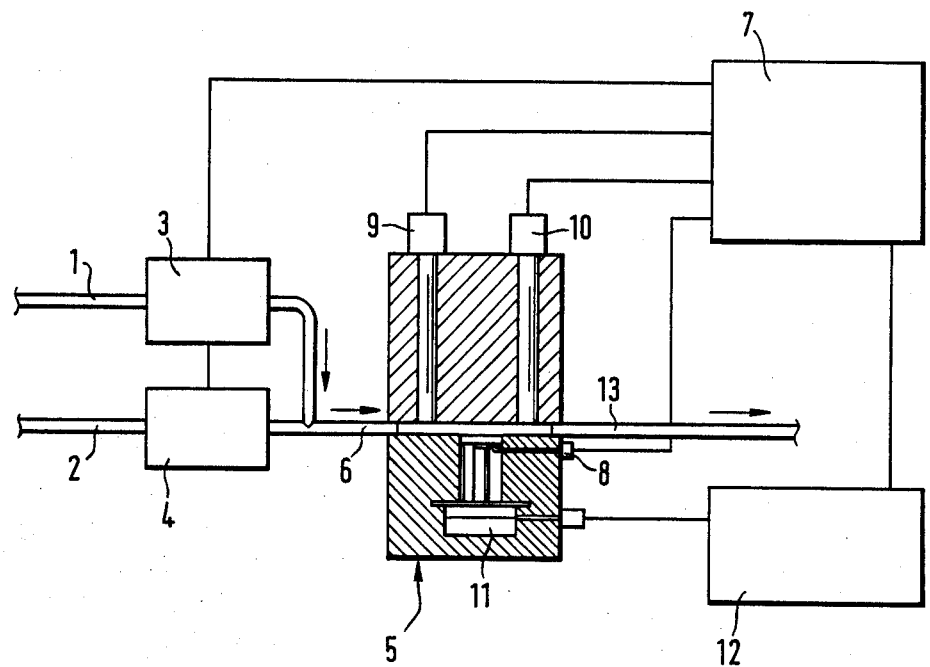
FIG. 1 is a schematical illustration of a measuring apparatus for carrying out a method according to a preferred embodiment of the invention.

According to FIG. 1, the reagent solution 1 and the solution for measurement 2, are conducted through the membrane pumps 3 and 4 into the common inlet pipe 6 of the measurement cell 5. The measurement cell 5 defines a solution space 16, and liquid introduced into the solution space by way of the inlet pipe 6 contacts a working electrode 8, a counter electrode 9 and a reference electrode 10. The three electrodes 8, 9 and 10 are electrically connected to a control and measurement unit 7. In order to generate ultrasound, an ultrasonic oscillator 12 is installed between the ultrasonic driving element 11 and the measurement unit 7. The measured solution is discharged from the measurement cell 5 through an outlet pipe 13.

The control and measurement unit comprises means for applying a selected potential between the counter electrode 9 and the reference electrode 10. In this manner, the potential of the working electrode 8 is adjusted. Generally, the working electrode is at a negative potential relative to the reference electrode. The unit 7 also comprises means for controlling operation of the pumps 3 and 4 and the oscillator 12, means for measuring the current flowing through the working electrode 8, and means for providing an output signal to a computer (not shown) representing the variation in current as a function of the voltage between the working electrode and the reference electrode.

Figure 2:
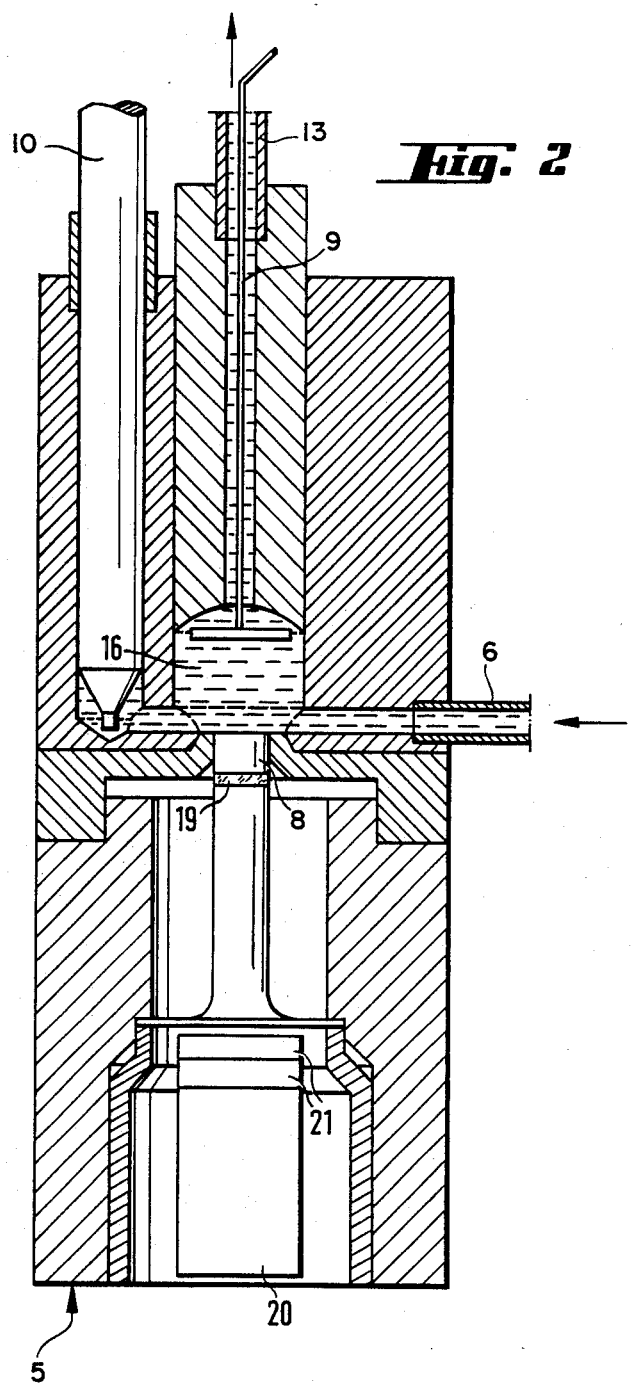
FIG. 2 is shows a cross-section view of the ultrasonic cell used in the FIG. 1 apparatus.

As shown in FIG. 2, the electrodes 8 and 9 are on opposite sides of the solution space 16. The working electrode 8 is a solid electrode, preferably made of glass carbon, and is installed on top of the glass sheet 19 so that thereby the working electrode 8 is in an essentially close connection to, and essentially in the same vertical plane as, the ultrasonic resonator 20 and the oscillating crystals 21. Therefore, the ultrasonic oscillations are of maximum amplitude at the surface of the working electrode 8. The outlet pipe 13 surrounds the counter electrode 9.

When carrying out anodic stripping analysis employing the measurement cell 5 of the invention, the unit 7 places the working electrode at a voltage $V_0$ relative to the reference electrode, and at time $t_0$ the ultrasound is switched on and the membrane pumps 3, 4 commence pulsated pumping of the solution for measurement, as well as the necessary reagents, into the inlet pipe 6 of the measurement cell. The flow pulses are preferably each of sufficient amplitude that the solution on the surface of the working electrode 8 and in the diffusion layer at the surface of the working electrode is completely replaced. At time $t_1$, towards the end of the preelectrolysis accumulation step and while the pulsated pumping and the ultrasound remain switched on, the voltage between the working electrode and the reference electrode is increased monotonically, at a substantially constant rate, until time $t_2$, when the voltage reaches a value $V_1$. At time $t_2$ the ultrasound and the pumping are switched off, but the voltage V continues to increase. The voltage $V_1$ is selected to be below the value at which current peaks are formed. The interval between the time $t_0$ and the time $t_2$ represents a preelectrolysis step, during which ions of substances to be determined are reduced at the surface of the working electrode during the preelectrolysis step, so that a significant guantity of these substances is accumulated on the surface of the working electrode. Also, atomic hydrogen is removed from the surface of the working electrode by the pulsating pumping and ultrasonic vibration of the working electrode. Consequently, the composition of the material in the immediate vicinity of the working electrode is the same as the composition of the material that has been introduced into the measurement cell by way of the pipe 6. Therefore, there is no layer of material covering the working electrode such as to interfere with the accuracy of the measurements that are made during the subsequent stripping step.

From the time $t_2$ to the time $t_3$, the voltage V continues to increase monotonically at a constant rate, and the current peaks are measured by means of the unit 7 during the interval from $t_2$ to the $t_3$. Because of the ultrasonic treatment, the concentration of atomic hydrogen on the surface of the working electrode and hence the background current due to oxidation of hydrogen is small. During the stripping step (time $t_2$ to time $t_3$) the substances accumulated on the surface of the working electrode in the preelectrolysis step re-enter solution at their respective characteristic voltages and the current peaks are thereby created.

At the time $t_3$, the voltage V attains the value $V_2$, which is selected to be above the value at which current peaks are formed for the substances of interest. The voltage V continues to increase monotonically after the time $t_3$, until at time $t_4$ it reaches the value $V_3$, but at the time $t_3$ the ultrasound and pumping are switched on once more. The voltage remains constant at the value $V_3$ until the time $t_5$. The interval from time $t_3$ to time $t_5$ is an elimination step, during which any residue of the substances that were reduced at the surface of the Working electrode 8 returns to solution and is thereby removed from the electrode surface, so that the electrode is regenerated. The voltage $V_3$ is selected to be sufficient that virtually all substances present on the surface of the working electrode are dissolved to the solution. After the elimination step has been completed, a new measurement can be made by repeating the sequence of operations that started at the time $t_0$.

Figure 3:
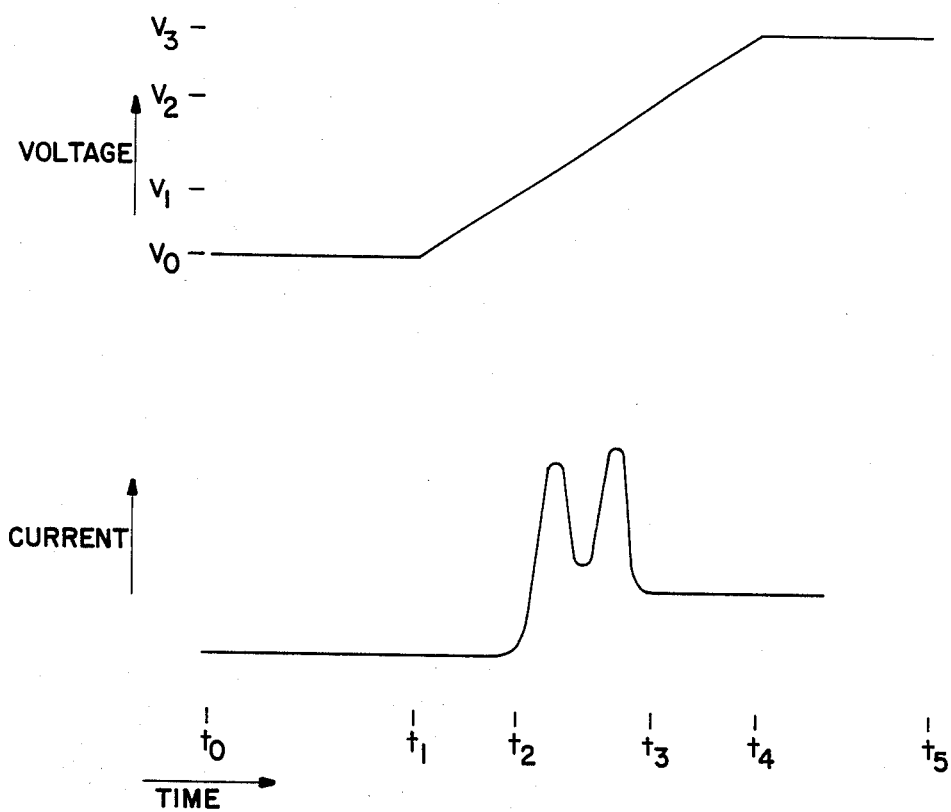
FIG. 3 is a graph illustrating variation of voltage potential and current with time.

If it is desired to use the automatic background elimination technique, which is as such known in the prior art, a normal stripping analysis measurement is first carried out in the manner described above with reference to FIG. 3, so that the solution current peaks are formed, and immediately thereafter a new measurement is carried out with the preelectrolysis step omitted. The voltammograms stored in the memory of the computer connected to the measurement unit 7 are subtracted, and consequently an automatically background-corrected voltammogram is obtained.

By use of the method described above, the measuring sensitivity is increased. Because the solution is agitated in the neighborhood of the electrode surface during the preelectrolysis step, hydrogen bubbles are removed from the electrode surface and the amount of atomic hydrogen decreases, and this improves the measurement conditions with respect to the substances that are deposited on the working electrode. Furthermore, the background current caused by the hydrogen oxidation is decreased at the current peaks. The pulsated solution transport allows for an effective elimination of the gas bubbles created on the electrode surface, which gas bubbles would otherwise disturb the measurements during the measurement step, i.e. during the formation of the current peaks.

By employing the voltammetric measuring method of the invention, the electrode surface remains active and the measurement results are stable. Furthermore, this method provides for the cleaning and stabilizing of the electrode surface. Consequently, if a thin film mercury electrode is used as the working electrode, the mercury film can be easily removed from the electrode surface without resorting to mechanical cleaning.

In the method described with reference to the drawings the invention is applied to an anodic stripping analysis, but it is naturally clear that the method of the invention, i.e. the use of ultrasound and the regulation of flow speed, can also be applied in other voltammetric measuring methods of anion and cation contents, without departing from the scope of the invention as defined in the appended claims and equivalents thereof.

EXAMPLE

As an applied example for the method of the patent application a determination of the $Fe^{3+}$-ion in aqueous solution is described.

The solution which is pumped by pulsating to the measurement cell, contains 0,1 molar concentration of potassium chloride (KCl) which has a pH value of 3,5.

The values of the voltage and the time for this solution for determination of the $Fe^{3+}$-ions are:

| Voltage mV SCE | | time | |
| --- | --- | --- | --- |
| | | $t_0$ | 0 |
| $V_0$ | −1800 | $t_1$ | 5 min |
| $V_1$ | −1000 | $t_2$ | 5 min 16 s |
| $V_2$ | 0 | $t_3$ | 5 min 36 s |
| $V_3$ | +1000 | $t_4$ | 5 min 56 s |

The current peak due to oxidation of iron during the measurement step is observed at −450 mV SCE.

We claim:

1. A stripping analysis method for analyzing a liquid using a measurement device that comprises wall means defining a measurement cell for receiving liquid to be analyzed, and also comprises a solid working electrode and a reference electrode that contact liquid in the cell, said method comprising the following steps, in the order stated:
    (a) a preelectrolysis step during which liquid to be analyzed is introduced into the measurement cell at a pulsating rate, the working electrode is vibrated at an ultrasonic frequency, and the voltage potential between the working electrode and the reference electrode is adjusted to a level which allows the substances to be determined to be deposited on the working electrode,
    (b) a stripping step during which the voltage potential between the working electrode and the reference electrode is scanned through the potential range where the substances to be determined are dissolved back to the liquid and current is measured while the liquid in the measurement cell remains essentially undisturbed, and
    (c) an elimination step during which the voltage potential between the working electrode and the reference electrode is adjusted to a level at which the working electrode is regenerated and the products of the measurement step are removed from the cell by vibrating the working electrode at an ultrasonic frequency and thereby disturbing the liquid in the cell, and introducing liquid into the cell at a non-pulsating rate and thereby displacing liquid from the cell.

2. An improved stripping analysis method for analyzing a liquid using a measurement device that comprises wall means defining a measurement cell for receiving a liquid to be analyzed, and also comprises a solid working electrode and a reference electrode that contact liquid in the cell, said method comprising the following steps, in the order stated:
    (a) a pre-electrolysis step during which liquid to be analyzed is introduced into the measurement cell and the voltage potential between the working electrode and the reference electrode is adjusted to a level which allows the substances to be determined to be deposited on the working electrode,
    (b) a stripping step during which the voltage potential between the working electrode and the reference electrode is scanned through the potential range where the substances to be determined are dissolved back to the liquid and current is measured while the liquid in the measurement cell remains essentially undisturbed, and
    (c) an elimination step during which the voltage potential between the working electrode and the reference electrode is adjusted to a level at which the working electrode is regenerated and the products of the measurement step are removed from the cell,
and wherein the improvement resides in that during the pre-electrolysis step the liquid to be analyzed is introduced into the measurement cell at a pulsating rate and the working electrode is vibrated at an ultrasonic frequency.

3. A method according to claim 2, wherein during the elimination step the products of the measurement step are removed from the cell by vibrating the working electrode at an ultrasonic frequency and thereby disturbing the liquid in the cell, and introducing liquid into the cell at a non-pulsating rate and thereby displacing liquid from the cell.

* * * * *